United States Patent
Wade

(10) Patent No.: US 10,426,465 B1
(45) Date of Patent: Oct. 1, 2019

(54) MECHANICAL, HOSE-LESS, CABLE-LESS, RE-USABLE DYNAMIC COMPRESSION BONE STAPLE DELIVERY DEVICE WITH ATTRIBUTES BUILT INTO HANDLE

(71) Applicant: Zimmer, Inc., Warsaw, IN (US)

(72) Inventor: Russell W. Wade, Laguna Niguel, CA (US)

(73) Assignee: Zimmer, Inc., Warsaw, IN (US)

( * ) Notice: Subject to any disclaimer, the term of this patent is extended or adjusted under 35 U.S.C. 154(b) by 750 days.

(21) Appl. No.: 14/796,971

(22) Filed: Jul. 10, 2015

Related U.S. Application Data

(60) Provisional application No. 62/023,043, filed on Jul. 10, 2014.

(51) Int. Cl.
*A61B 17/068* (2006.01)
*A61B 17/064* (2006.01)
*A61B 17/072* (2006.01)

(52) U.S. Cl.
CPC ...... *A61B 17/0682* (2013.01); *A61B 17/0642* (2013.01); *A61B 2017/07271* (2013.01)

(58) Field of Classification Search
CPC ..... A61B 17/10; A61B 17/115; B25C 5/0235; B25C 5/025; B25C 5/0285; B25C 5/0292; B25C 5/11; B25C 5/1617; B25C 5/162
See application file for complete search history.

(56) References Cited

U.S. PATENT DOCUMENTS

| | | | |
|---|---|---|---|
| 6,755,338 B2 * | 6/2004 | Hahnen | A61B 17/07207 227/175.1 |
| 8,523,040 B2 * | 9/2013 | Crainich | A61B 17/0401 227/175.1 |

* cited by examiner

*Primary Examiner* — Anu Ramana
(74) *Attorney, Agent, or Firm* — Schwegman Lundberg & Woessner, P.A.

(57) ABSTRACT

A device for deploying a staple into desired bone has a staple cartridge for retaining a bone staple and a spring-loaded plunger shaft having a distal end proximal to the bone staple, the plunger shaft being retained in a proximal orientation by a latch. Squeezing a trigger releases the latch, so that the plunger shaft moves to its distal position, striking the staple and deploying the staple distally into a bone site. An additional method step, in the event that one wishes to deploy a differently sized staple, involves detaching the staple cartridge from the device and attaching a differently-sized staple cartridge to the device.

17 Claims, 4 Drawing Sheets

MECHANICAL, HOSE-LESS, CABLE-LESS, RE-USABLE DYNAMIC COMPRESSION BONE STAPLE DELIVERY DEVICE WITH ATTRIBUTES BUILT INTO HANDLE

This application claims the benefit under 35 U.S.C. 119(e) of the filing date of Provisional U.S. Application Ser. No. 62/023,043, entitled Mechanical, Hose-Less, Cable-Less, Re-Usable Dynamic Compression Bone Staple Delivery Device with Attributes Built Into Handle, filed on Jul. 10, 2014, which application expressly incorporated herein by reference, in its entirety.

This application is also related to U.S. Pat. No. 6,059,787 entitled Compression Bone Staple, Apparatus and Method, issued May 9, 2000, to U.S. Pat. No. 6,348,054 entitled Compression Bone Staple, Apparatus and Method, issued Feb. 19, 2002, to U.S. Pat. No. 6,783,531 entitled Compression Bone Staple, Apparatus and Method, issued Aug. 31, 2004, and to U.S. patent application Ser. No. 13/745,651, now U.S. Pat. No. 10,064,618 filed on Jan. 18, 2013, entitled Compression Bone Staple, Apparatus and Method, all of which are commonly assigned and expressly incorporated herein, by reference, in their entirety.

BACKGROUND OF THE INVENTION

In treating a bone fracture it is common practice to fasten one bone segment to the other so as to stabilize and immobilize them for the duration of the bone consolidation process. Thus there is the technique of internal fixation or direct mechanical fastening of the bone segments. Traditionally, fixation has been accomplished by variety of apparatus and techniques, the more common involving the use of metallic fastening devices such as screws, connector plates (secured to the bone by screws), pins and clips. These methods invariably involve the drilling of screw holes in the bone and the use of related equipment such as drill hole templates. In view of the limitations of the afore-mentioned methods, stapling has been looked to as a way to produce compression.

Pneumatic compression bone staple delivery devices with an air hose/cable connected to the handle to provide needed pneumatic pressure to the delivery device are known in the industry. However, a mechanical, hose-less, dynamic compression bone staple delivery device with attributes built into the handle will add additional options for orthopedic surgeons.

SUMMARY OF THE INVENTION

A compression bone staple delivery device mechanism with attributes built into the handle has no hoses or cables, It can be serialized and re-used. A universal coupling feature allows for various staple types and sizes to be used, and adds additional options for hospitals, surgery centers, podiatrists, and orthopedic surgeons.

More particularly, there is provided a compression bone staple delivery system, which comprises a housing, a handle attached to the housing, and a shaft disposed within the housing, movable between proximal and distal orientations and positioned so that a distal end of the shaft impacts a staple retained on a distal end of the housing for deploying the staple distally into a desired bone site when the shaft is moved from a proximal orientation to a distal orientation. A spring is provided for biasing the shaft toward its distal orientation. A latch is provided for restraining the shaft in a proximal orientation. A latch release is actuatable to move the latch to a non-restraining orientation so that the shaft moves to its distal orientation, thereby deploying the staple disposed on the housing.

The spring comprises a compression spring captured between a proximal end of the shaft and a proximal end of the housing in a compressed orientation so that energy is stored for release to drive the shaft distally when the latch is disengaged from the shaft by the latch release. In the disclosed embodiment, the latch comprises a pawl for engagement with the shaft, and the latch release comprises a trigger for moving the pawl. A second compression spring is provided for biasing the pawl in its retaining orientation. Additionally, as a further safety factor, a torsion spring is provided for biasing the trigger against its latch release orientation.

A plunger is connected to a proximal end of the shaft, and a plunger knob is actuatable proximally to retract the shaft in a proximal direction. A coupling is attached to a distal end of the housing for retaining a staple cartridge. The coupling comprises a proximal mounting portion for attaching the coupling to a distal end of the housing. A staple cartridge is disposed on the coupling. The staple cartridge comprises a retainer portion having a concave recess for receiving a bridge of a staple. The staple cartridge further comprises a lower portion for attaching the staple cartridge to the coupling. The coupling is adapted to retain interchangeable staple cartridges of differing sizes.

In another aspect of the invention, there is disclosed a method of deploying a bone staple into a desired bone site, which comprises a step of locating a bone staple delivery device adjacent to a desired bone site. The located device has a coupling for retaining a bone staple thereon with the bone staple disposed at a distal end of the device, directly adjacent to the bone site, and further comprises a spring-loaded plunger shaft having a distal end proximal to the bone staple, the plunger shaft being retained in a proximal position by a latch. A further step of the inventive method involves actuating a latch release, so that the plunger shaft moves to its distal position, striking the staple and deploying the staple distally into the bone site.

The coupling is adapted to retain a staple cartridge thereon, the staple cartridge holding a staple therein. In the event that a practitioner wishes to deploy a differently sized staple, a further method step involves detaching the staple cartridge from the coupling and attaching a differently-sized staple cartridge thereto.

In the disclosed method, the latch release comprises a trigger, and the step of actuating the latch release comprises squeezing the trigger.

The invention, together with additional features and advantages thereof, may best be understood by reference to the following description taken in conjunction with the accompanying illustrative drawings.

DESCRIPTION OF THE PREFERRED EMBODIMENT

Figure 1:
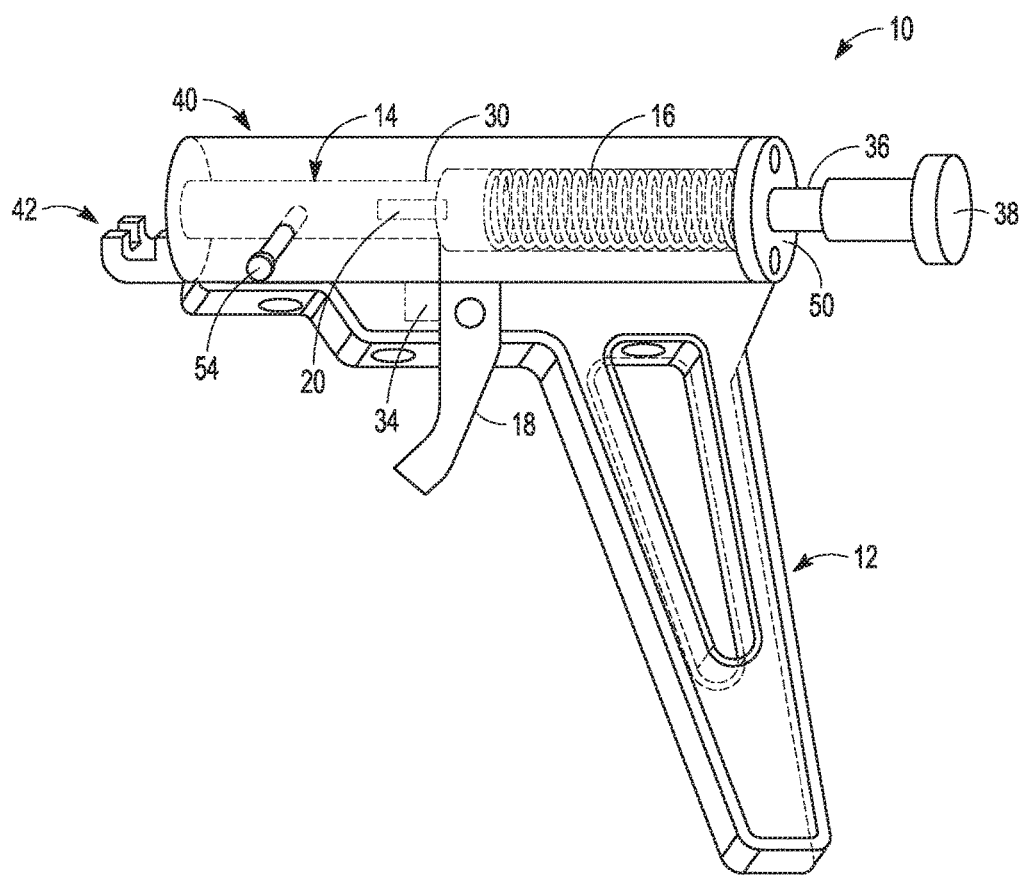
FIG. 1 is a top isometric view of a compression bone staple delivery device constructed in accordance with the principles of the present invention, with a staple and safety retainer in place.
Figure 2:
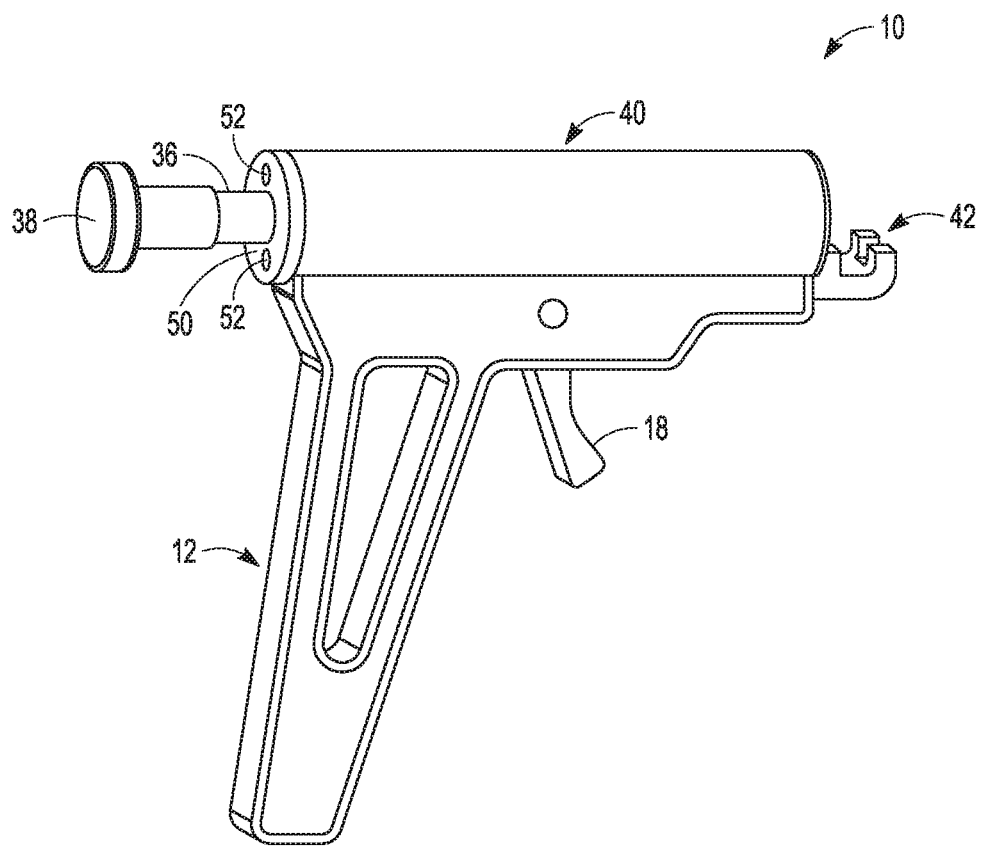
FIG. 2 is a bottom isometric view of the compression bone staple delivery device of FIG. 1.
Figure 3:
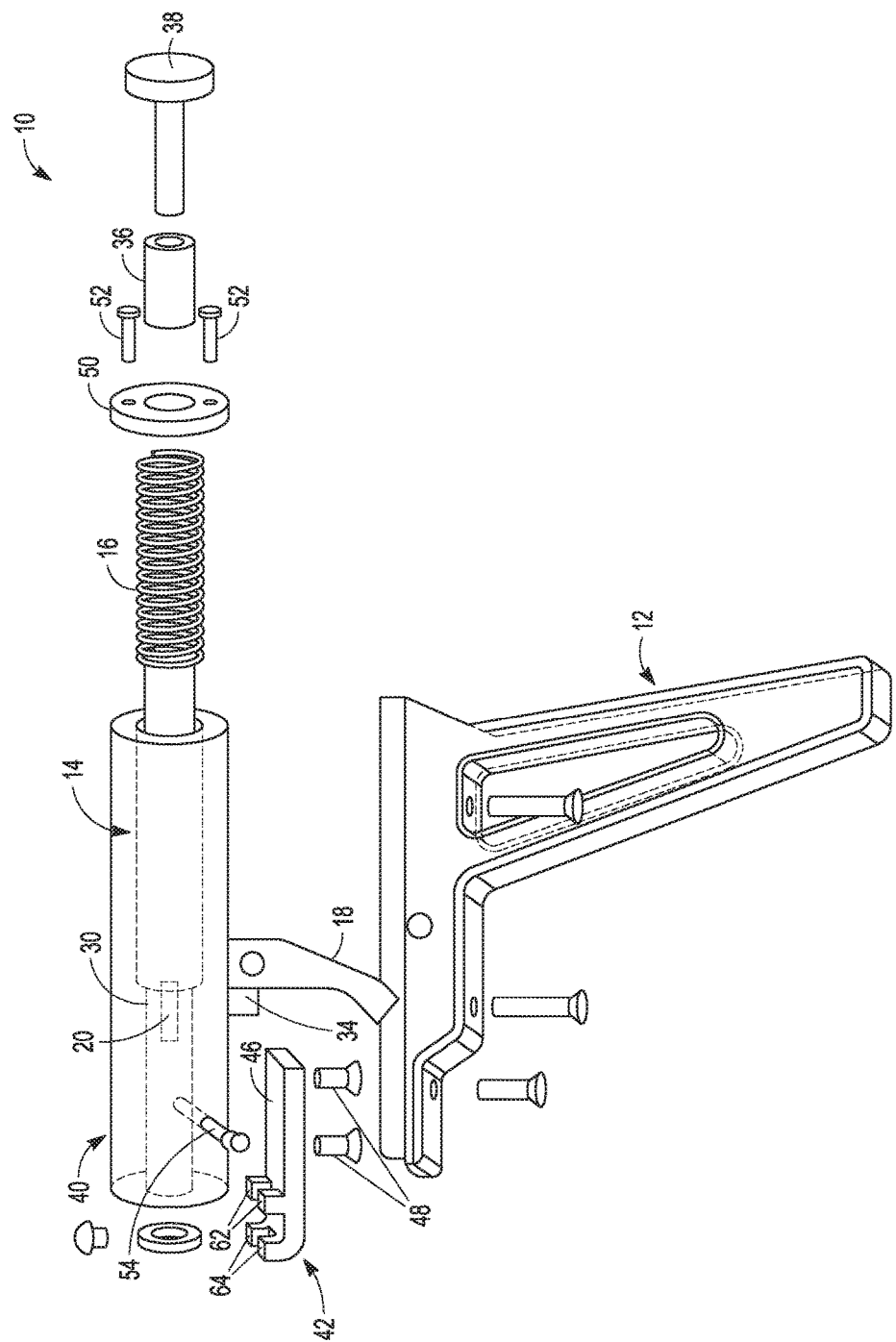
FIG. 3 is an exploded isometric view of the compression bone staple delivery device of FIGS. 1 and 2.

Referring more particularly to the drawings, there is shown in FIGS. 1-3 a compression bone staple delivery device 10, which comprises a handle 12 for a grasping and containing mechanism, and a shaft 14 for striking and delivering a staple. A compression spring 16 provides force to the shaft 14 for delivering the staple. A trigger 18 is provided for actuating a latching system 20. A spacer provides space for a finger and a hard stop when the trigger 18 is activated. The latching system 20 functions to retain the spring-loaded shaft 14 in position until it is desired to deploy a staple 22 into bone, at which point the trigger 18 is actuated by a practitioner to withdraw the latch and thereby release the shaft to be pushed distally by forces applied by the compression spring 16.

The staple 22 may be constructed as is disclosed in any of commonly assigned U.S. Pat. Nos. 6,059,787, 6,348,054, or 6,783,531, or in U.S. patent application Ser. No. 13/745,651, for example, all of which have already been expressly incorporated herein by reference, and may comprise a pair of legs 24, 26, respectively, joined by a bridge 28 (see FIG. 4). The staple 22 will not be further described herein, because the purpose of this application is to describe and claim an inventive staple delivery device 10, and it is suitable for use with any bone staple.

As shown in the drawings, the latching system 20 comprises a pawl 30, which, in its ordinary retaining orientation, is positioned to prevent distal movement of the shaft 14. A compression spring 32 biases the pawl in its retaining orientation, and a torsion spring 34 biases the trigger against actuation, to ensure that there is no inadvertent actuation of the shaft, and thereby premature deployment of the staple.

A plunger 36 is connected to a proximal end of the shaft 14, providing yet one more safeguard against inadvertent activation of a staple. A plunger knob 38 is provided for retracting the plunger 36 and its attached shaft 14, and particularly for retracting and loading the shaft prior to activation.

A housing 40 contains and provides primary support for the device mechanisms, including the shaft 14, compression spring 16, and latching system 20, and also provides primary support for the handle 12 and a coupling 42 for holding a bone staple cartridge 44 (FIG. 4) and a rest during staple delivery. The housing 40 also provides guidance for the latching system 20 and the plunger 36.

The coupling 42 includes a proximal mounting portion 46 (FIG. 3), by which the coupling 42 is attached to a distal end of the housing 40 via fasteners 48. A ball plunger is provided, for centering the bone staple cartridge 44 with tactile feel.

An end plate 50, secured to a proximal end of the housing by fasteners 52, functions to retain compression spring loads.

A PTFE seal, which is a liquid seal, is provided for preventing fluid from entering the housing 40. A retainer is provided for retaining spring pressure during pre-load and loaded conditions. A set screw 54 is provided for ensuring anti-rotation of the shaft 14, including an extended point that slides in a slot in the shaft.

Figure 4:
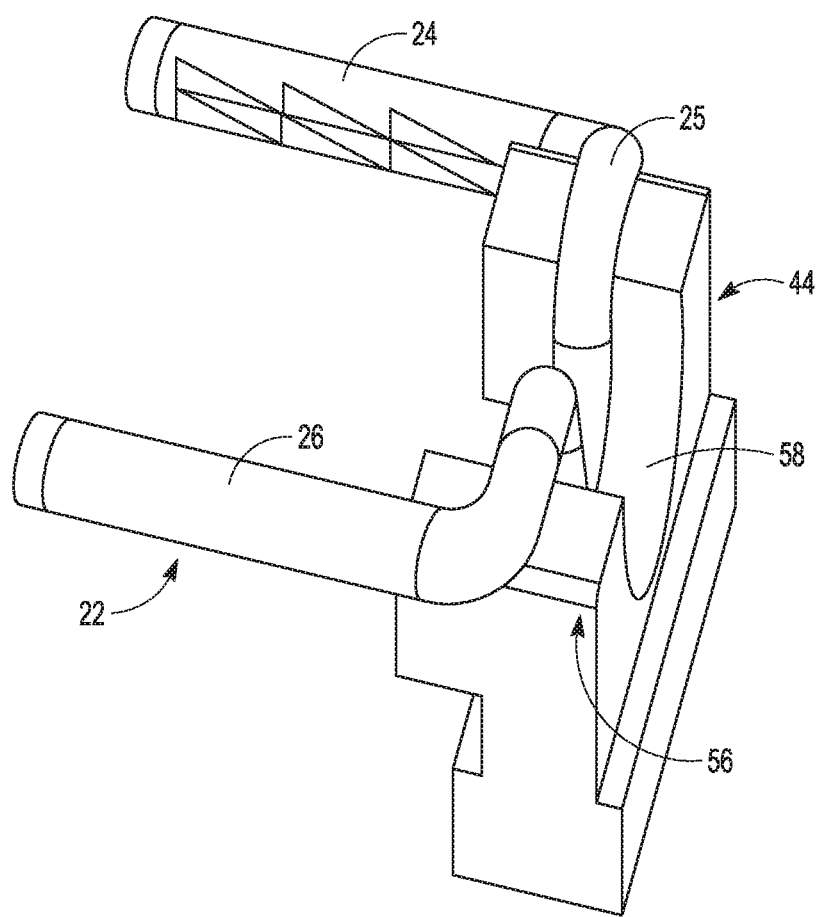
FIG. 4 is an isometric view of a staple guide for use with the compression bone staple delivery device of FIGS. 1-3.

The staple cartridge 44, as noted above, is provided for receiving and retaining a staple 22 thereon, and for guiding the staple 22 into pre-drilled holes in bone. The staple cartridge 44 includes a retainer portion 56 having a concave recess 58 for receiving the bridge 28 of a staple 22, as shown in FIG. 4, and a lower portion 60 for attaching the staple cartridge 44 to the coupling 42, by securing the cartridge 44 between proximal flanges 62 and distal flanges 64 on the coupling 42.

The staple guide 44 has guide features, which may comprise channels matching the configuration of legs 22, 24, included on the retainer portion 56 thereof, that allow a staple 22 to slide in place during assembly, and to slide off when deployed. The device 10 can be manufactured to accommodate a variety of 100 common staples by installing different staple cartridges 44 which are each configured specifically for use with one particular size staple. Small staples will have matching small cartridges 44 and large staples will have matching large cartridges 44.

Accordingly, although exemplary embodiments of the invention have been 105 shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A compression bone staple delivery system, comprising:
   a housing;
   a handle attached to the housing;
   a shaft disposable within the housing, movable between a proximal orientation and a distal orientation and positionable so that a distal end of the shaft impacts a staple for deploying the staple distally into a desired bone site when the shaft is moved from the proximal orientation to the distal orientation;
   a spring configured to bias the shaft toward the distal orientation;
   a latch configured to retain the shaft in the proximal orientation;
   a coupling attachable to a distal end of the housing;
   a staple cartridge housed within the coupling; and
   a latch release, the latch release being actuatable to move the latch to a non-restraining orientation so that the shaft moves to the distal orientation, thereby deploying the staple from a position in the staple cartridge into the desired bone site.

2. The system as recited in claim 1; wherein the spring comprises a compression spring captured between a proximal end of the shaft and a proximal end of the housing in a compressed orientation so that energy is stored for release to drive the shaft distally when the latch is disengaged from the shaft by the latch release.

3. The system as recited in claim 1; wherein the latch comprises a pawl for engagement with the shaft, and the latch release comprises a trigger for moving the pawl.

4. The system as recited in claim 3, and further comprising a compression spring for biasing the pawl to retain the shaft in the distal orientation.

5. The system as recited in claim 4, and further comprising a torsion spring for biasing the trigger against moving the pawl to release the shaft.

6. The system as recited in claim 1, and further comprising a plunger connectable to a proximal end of the shaft, and a plunger knob which is actuatable proximally to retract the shaft in a proximal direction.

7. The system as recited in claim 1, wherein the coupling comprises a proximal mounting portion configured to attach the coupling to the distal end of the housing.

8. The system as recited in claim 1, wherein the staple cartridge comprises a retainer portion having a concave recess configured for receiving a bridge of a staple.

9. The system as recited in claim 1, wherein the staple cartridge comprises a lower portion configured for attaching the staple cartridge to the coupling.

10. The system as recited in claim 1, wherein the coupling is configured to retain interchangeable staple cartridges of differing sizes.

11. A compression bone staple delivery system, comprising:
- a housing;
- a handle attached to the housing;
- a shaft disposable within the housing, movable between a proximal orientation and a distal orientation and positionable so that a distal end of the shaft impacts a staple for deploying the staple distally into a desired bone site when the shaft is moved from the proximal orientation to the distal orientation;
- a spring configured to bias the shaft toward the distal orientation;
- a pawl configured for engagement with and restraining the shaft in the proximal orientation;
- a coupling attachable to a distal end of the housing;
- a staple cartridge configured to be housed within the coupling;
- a trigger, the trigger being actuatable to move the pawl to a non-restraining orientation so as to allow the shaft to move to the distal orientation, thereby deploying the staple from a position in the staple cartridge into the desired bone site; and
- a compression spring configured for biasing the pawl to retain the shaft in the distal orientation.

12. The system as recited in claim 11, and further comprising a torsion spring configured for biasing the trigger against moving the pavvl to release the shaft.

13. The system as recited in claim 11 and further comprising a plunger connectable to a proximal end of the shaft, and a plunger knob which is actuatable proximally to retract the shaft in a proximal direction.

14. The system as recited in claim 11, wherein the coupling comprises a proximal mounting portion configured for attaching the coupling to the distal end of the housing.

15. The system as recited in claim 14, wherein the coupling is configured to retain interchangeable staple cartridges of differing sizes.

16. The system as recited in claim 14, wherein the staple cartridge comprises a retainer portion having a concave recess configured for receiving a bridge of a staple.

17. The system as recited in claim 14, wherein the staple cartridge comprises a lower portion configured for attaching the staple cartridge to the coupling.

* * * * *